United States Patent
Kravitz et al.

(10) Patent No.: US 10,258,032 B2
(45) Date of Patent: Apr. 16, 2019

(54) TRANSPORTATION BAG FOR USE WITH AN ORGAN TRANSPORTER

(75) Inventors: David C. Kravitz, Barrington Hills, IL (US); Peter DeMuylder, Londerzeel (BE); Brian Otts, Warrior, AL (US); Stephan Merkle, Chicago, IL (US); Jeremiah P. O'Leary, Chicago, IL (US); Christopher E. Svensrud, Chicago, IL (US)

(73) Assignee: LIFELINE SCIENTIFIC, INC., Itasca, IL (US)

(*) Notice: Subject to any disclaimer, the term of this patent is extended or adjusted under 35 U.S.C. 154(b) by 220 days.

(21) Appl. No.: 13/348,195

(22) Filed: Jan. 11, 2012

(65) Prior Publication Data

US 2013/0177897 A1 Jul. 11, 2013

(51) Int. Cl.
*A01N 1/02* (2006.01)
*A61B 10/00* (2006.01)

(52) U.S. Cl.
CPC ........ *A01N 1/0273* (2013.01); *A61B 10/0096* (2013.01)

(58) Field of Classification Search
CPC ................ A01N 1/0273; A61B 10/0096
USPC ............................. 435/283.1–9.43
See application file for complete search history.

(56) References Cited

U.S. PATENT DOCUMENTS

| | | | |
|---|---|---|---|
| 5,253,739 A * | 10/1993 | King | A45C 5/14 190/115 |
| 5,285,657 A | 2/1994 | Bacchi et al. | |
| 5,628,204 A | 5/1997 | Shanaberger | |
| 6,490,880 B1 | 12/2002 | Walsh | |
| D468,436 S | 1/2003 | Brassil et al. | |
| D470,594 S | 2/2003 | Brassil et al. | |
| 6,673,594 B1 * | 1/2004 | Owen et al. | 435/284.1 |
| 7,634,919 B2 | 12/2009 | Bernhard, Jr. et al. | |
| 7,691,622 B2 | 4/2010 | Garland et al. | |
| 7,775,388 B2 | 8/2010 | Murrer, III | |

(Continued)

FOREIGN PATENT DOCUMENTS

| | | |
|---|---|---|
| CN | 101208568 A | 6/2008 |
| DE | 602006000159 T2 | 7/2008 |

(Continued)

OTHER PUBLICATIONS

Jan. 21, 2014 Written Opinion issued in International Patent Application No. PCT/US2013/020286.

(Continued)

*Primary Examiner* — Gautam Prakash
*Assistant Examiner* — Lydia Edwards
(74) *Attorney, Agent, or Firm* — Oliff PLC

(57) ABSTRACT

A bag includes an organ transporter compartment to contain an organ transporter disposed in the transporter compartment. The bag may include openings to access portions of the organ transporter, such as a battery or power cable, when the organ transporter is disposed in the bag. The bag may also include a frame and handles. The handles may include structure adapted to mate with handles on the organ transporter. The bag may also include a single cover that provides access to multiple compartments with their own internal covers. Also, the bag may include windows to view documents stored in the bag and/or to view and/or display control panels on the organ transporter.

18 Claims, 9 Drawing Sheets

(56) References Cited

U.S. PATENT DOCUMENTS

| | | | |
|---|---|---|---|
| 2004/0235142 A1* | 11/2004 | Schein | A01N 1/02 435/284.1 |
| 2005/0285715 A1 | 12/2005 | Comunale | |
| 2007/0028642 A1* | 2/2007 | Glade et al. | 62/371 |
| 2007/0184545 A1* | 8/2007 | Plaats | A01N 1/02 435/284.1 |
| 2010/0252598 A1* | 10/2010 | Cragg | 224/579 |
| 2011/0033916 A1 | 2/2011 | Hutzenlaub et al. | |
| 2012/0145754 A1* | 6/2012 | Green | 224/158 |

FOREIGN PATENT DOCUMENTS

| | | | |
|---|---|---|---|
| EP | 1 688 124 A1 | 8/2006 | |
| WO | WO 2006/124149 A2 | 11/2006 | |
| WO | 2009/041806 A1 * | 4/2009 | |

OTHER PUBLICATIONS

U.S. Appl. No. 29/410,727, filed Jan. 11, 2012.
Sep. 11, 2014 Communication issued in European Patent Application No. 13700795.1.
Jul. 21, 2015 Office Action issued in Chinese Application No. 201380004617.4.
May 5, 2016 Office Action issued in Chinese Patent Application No. 201380004617.4.
Apr. 8, 2014 International Report on Patentability issued in International Patent Application No. PCT/US2013/020286.

* cited by examiner

TRANSPORTATION BAG FOR USE WITH AN ORGAN TRANSPORTER

BACKGROUND

Various devices have been developed for the transportation of organs or other tissue. Some such devices are also capable of perfusion of the organ or tissue at warm and/or cold temperatures to extend the useful life of the organ.

For example, U.S. Pat. No. 6,673,594, which is hereby incorporated by reference in its entirety, discloses various systems and methods that may be involved in an organ transporter with perfusion capability. U.S. Design Pat. No. D 470,594, which is hereby incorporated by reference in its entirety, shows the external configuration of an exemplary organ transporter.

SUMMARY

Exemplary implementations improve transportation aspects of organ transporters. For example, exemplary implementations permit association of other items, such as transplant records, tissue samples, fluid samples, and/or back-up equipment for the transporter (such as a battery or power cable) with the organ transporter during transport, so that these items are readily available and/or do not become lost.

Exemplary implementations provide a flexible or partially flexible container (hereinafter "bag") for use with an organ transporter. The bag may include a compartment adapted for holding the organ transporter. Such a compartment may include a first closable opening configured for insertion and removal of the organ transporter. The compartment may also include a second opening that allows access from outside the bag to a removable battery and/or power cord of the organ transporter while the organ transporter is in the compartment holding the organ transporter. The bag may also or alternatively include a compartment, accessible from outside of the bag, for additional storage, preferably storage of spare components for the organ transporter such as a battery and/or power cord.

Exemplary implementations provide a bag with at least two externally accessible handles and/or an internal frame that is preferably less flexible than other features of the bag, and may be quite stiff or even rigid. The handles may also be rigid. The handles may be rigidly connected to the frame. At least one of the handles may be configured to mate with and/or secure a handle that is on an external surface of the organ transporter when the organ transporter is disposed in the bag. At least one of the handles may also include structure to facilitate tying down the bag and/or structure to provide ventilation for exchange of air that facilitates dissipation of heat generated by the organ transporter. Additional flexible or rigid handles may also be provided.

Exemplary implementations provide a bag that includes at least one window adapted to allow viewing of controls and/or a display on an organ transporter while the organ transporter is disposed in the bag.

Exemplary implementations include a bag with a compartment for storage of samples, such as tissue and/or fluid samples, that is separate from the compartment for storing the organ transporter. Preferably, both the sample compartment and the organ transporter compartment include separately openable and closeable covers. The bag may also include a third openable and closeable cover that provides access to the covers for the sample compartment and the organ transporter compartment. The third openable and closeable cover may include one or more optionally windowed compartments for the storage and display of documents. Preferably, such windowed compartments are openable and closeable from one or both of the inside and the outside of the third openable and closeable cover.

DETAILED DESCRIPTION OF EMBODIMENTS

While apparatus and methods described herein are particularly useful as bags for organ transporters, apparatus and methods described herein may also be used in various other applications. Thus, the apparatus and methods described herein are not limited to the applications described below in conjunction with the exemplary implementations.

Figure 1:
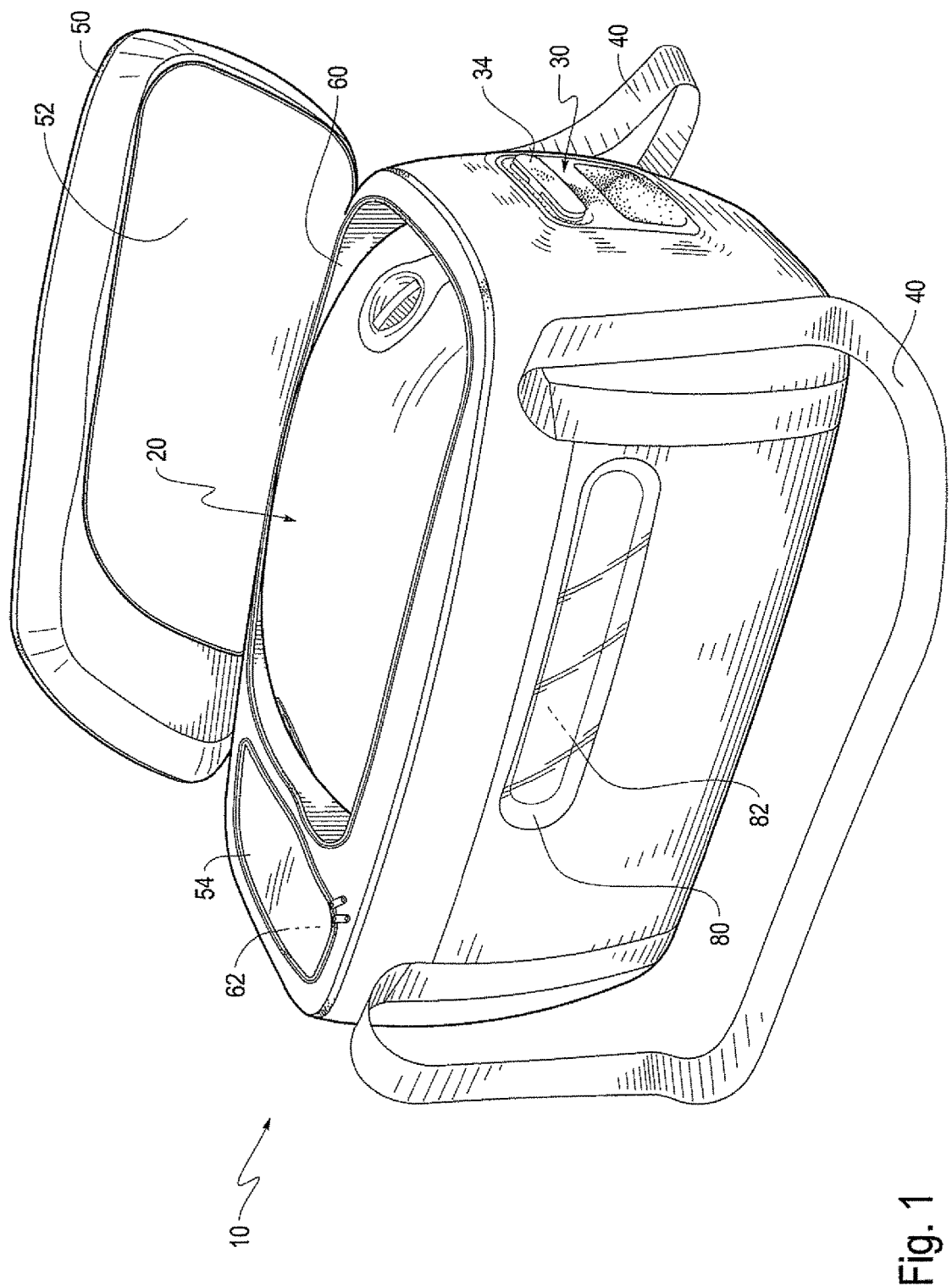
FIG. 1 illustrates a bag in an open state with a transporter therein.

FIG. 1 shows a bag 10 with an organ transporter 20 disposed therein. The bag 10 may include a rigid handle 30, preferably two or more rigid handles, preferably disposed on opposite ends of the bag 10. Wheels on one or both ends of the lower portion of the bag may be provided. The bag 10 may also include at least one flexible handle 40 (shown in FIGS. 1, 3, 5-7 and 9), with two such flexible handles 40 being shown on opposite sides of the bag 10. Of course, no handles or any number of flexible handles are contemplated by exemplary implementations disclosed herein. For example, a single flexible handle 40 can be implemented. Long flexible handles 40 as shown can be used as shoulder straps so that a single user can comfortably carry the bag 10. The flexible handles 40 are shown as attached to the bag 10, but may also be removable through the use of hooks, loops or other fastening structure.

An outer shell of the bag 10 may be composed of flexible or semi-rigid fabric to allow the bag to conform to its contents or so that the bag 10 may stand open or be partially collapsed when the organ transporter 20 or other contents are not disposed in the bag 10.

The bag 10 may include an outer lid or cover 50, which is shown in an open state in FIG. 1. The cover 50 may be hinged as shown or completely removable. Inside of the outer cover 50 there may be a first inner cover 52 and a second inner cover 54. FIG. 1 shows the first inner cover 52 in an open configuration and the second inner cover 54 in a closed configuration. The first inner cover 52 provides access to an organ transporter compartment 60. The organ transporter compartment 60 may be adapted for loose or preferably snug containment, storage, and/or transport of the organ transporter 20, and the first inner cover 52 may be loosely or snugly sized to accommodate insertion and removal of the organ transporter 20.

The second inner cover 54 may provide access to a compartment such as a sample compartment 62. The sample compartment 62 may be adapted for storage and transport of fluid or tissue samples and/or fluid or tissue sample containers related to an organ that is contained in the organ transporter 20. Although not shown, suitable structures may be included within the sample compartment 62 for securing items stored in the compartment. For example, straps, tie-downs and/or dividers may be provided in the sample compartment 62. The sample compartment 62 may be made of materials that are washable. To facilitate washing, the entire sample compartment 62 may be removable from the bag 10. The sample compartment 62 may also include structures suitable to receive cooling elements, which may be included if samples are to be stored in a cold state. The sample compartment 62 may also be made of a thermally insulating material.

The first inner cover 52 and second inner cover 54 may be opaque or transparent, although they are shown in the figures as opaque.

Figure 2:
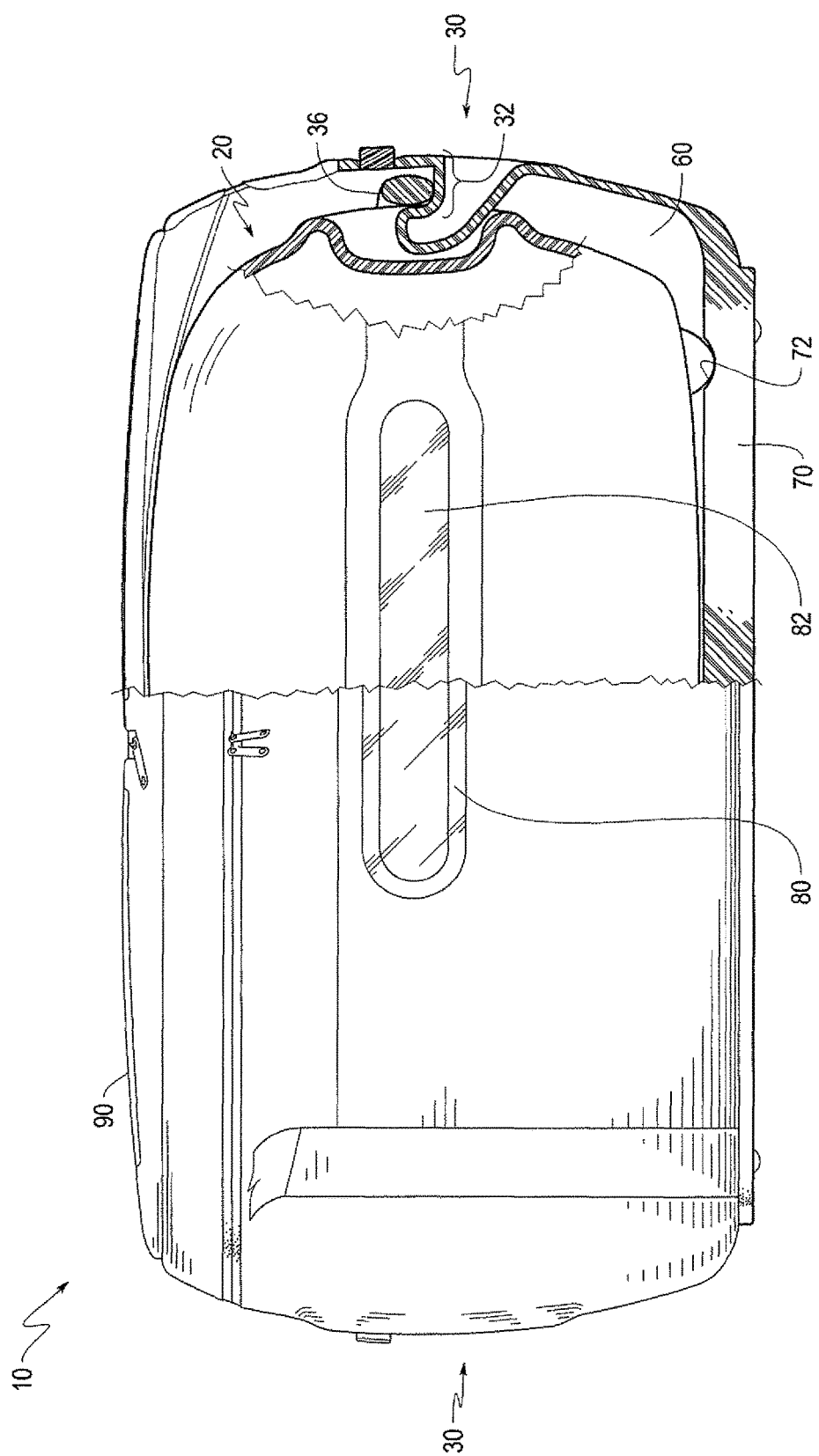
FIG. 2 illustrates a partial cross section of a bag with a transporter therein.

A rigid handle 30 is shown in FIGS. 1-3, 5-7 and 9. FIG. 2 shows a partial cross section view of the bag 10 with the organ transporter 20 disposed in the organ transporter compartment 60. The organ transporter 20 is also shown in a partial cross section to illustrate a preferred interface between the bag 10 and the transporter 20. A portion of the handle 30 may include a generally U-shaped portion 32, which may be configured to support and/or mate with a handle 36, or other load-bearing member, of the organ transporter 20. Such a U-shaped portion 32 or similar structure may be provided to help secure the organ transporter 20 within the organ transporter compartment 60. Such structure not only helps to secure the organ transporter 20, but also ensures that loads will be applied to the handle 36 of the organ transporter 20 as intended. Although not shown, a similar interface for a handle on an opposite end of the organ transporter 20 may be provided. The structure may be part of the handle 30 (opposite to the handle 30 shown in cross section) or the structure may be separate from the handle 30.

As shown in FIG. 2, the handle 30 may protrude into the bag 10 and form ergonomic surfaces (which include U-shaped portion 32) for a user to insert one or more fingers. Such a handle 30 with internal gripping surfaces may be advantageous in that they may be less likely to provide obstructions or protrusions that would undesirably catch the bag 10 on an external object. However, externally formed handles may also be provided. The internally extending surfaces of the handle 30 may be flexible or partially flexible to enhance mating with handles of the transporter.

The bag 10 may include a rigid or semi-rigid internal frame. The frame may be completely internal to the bag 10, completely external to the bag 10, or partially internal and partially external to the bag 10. Some portions of the frame may form an external surface of the bag 10. As shown throughout the figures, the frame is preferably mostly internal to the bag 10 and therefore is referred to hereinafter as the internal frame 70; however, this is not intended to be limiting. The internal frame 70 may be provided along a bottom of the bag 10, and may form all or part of a bottom surface of the bag 10. The internal frame 70 may provide a platform upon which the organ transporter 20 may be placed. Such a platform may help to protect the organ transporter 20 from damage due to an accidental drop. The internal frame 70 may include indentations 72 that mate with feet on the organ transporter 20, which can provide additional structure to positively locate and/or support the organ transporter 20. The internal frame 70 may be continuous and sheet-like, may include open spaces to reduce weight, and/or may be formed of interlocking rods, tubes or bars to provide rigidity with reduced weight.

The internal frame 70 is shown as a piece that is continuous with the handle 30, but other exemplary implementations are also contemplated. For example, the frame 70 and handle 30 may be composed of multiple interlocking pieces, or the frame 70 and handle 30 may be separate and distinct, with the handle 30 and frame 70 preferably being fastened to an outer wall of the bag 10 to provide positive location for the frame 70 and handle 30. If the frame 70 and handle 30 are a continuous piece, improved stability of the bag 10 as well as the organ transporter 20 within the bag 10 may be achieved. The frame 70 and the handle 30 may be manufactured by any suitable method, but these components may be particularly suited to manufacture by injection molding and may be injection molded as a single piece.

FIGS. 1-4, 6 and 7 also show a transparent window 80 which may be included in exemplary implementations. One or more window 80 may be adapted to allow a user to view a display panel 82 and/or control panel that is part of the organ transporter 20. Preferably, the window 80 is configured to allow a user to view the display panel 82 when the organ transporter 20 is disposed in the organ transporter compartment 60.

FIGS. 2-8 show two windows 90 that allow viewing internal contents of at least one compartment (not labeled), which may be included in exemplary implementations. Any number of compartments may be included, and, as shown, there may be a single large compartment, or separate compartments behind each window. One or more walls may be provided behind the windows 90, or the walls may be omitted so that an interior of the bag 10 is visible. If a wall is provided, the wall may be made from an opaque material (for example, fabric) or a transparent material similar to the windows 90 so that an interior of the bag is visible. Although two such windows 90 are shown, any number of windows 90 may be included as needed. Such windows 90 and compartment(s) may be used to store, in a viewable manner, important documents related to storage and/or transport of an organ in the organ transporter 20. By placing documents behind windows 90, the documents can readily be viewed as needed by a user, but the documents will remain safe and secure without need for a user to be concerned about the documents being lost or damaged during transport.

Figure 3:
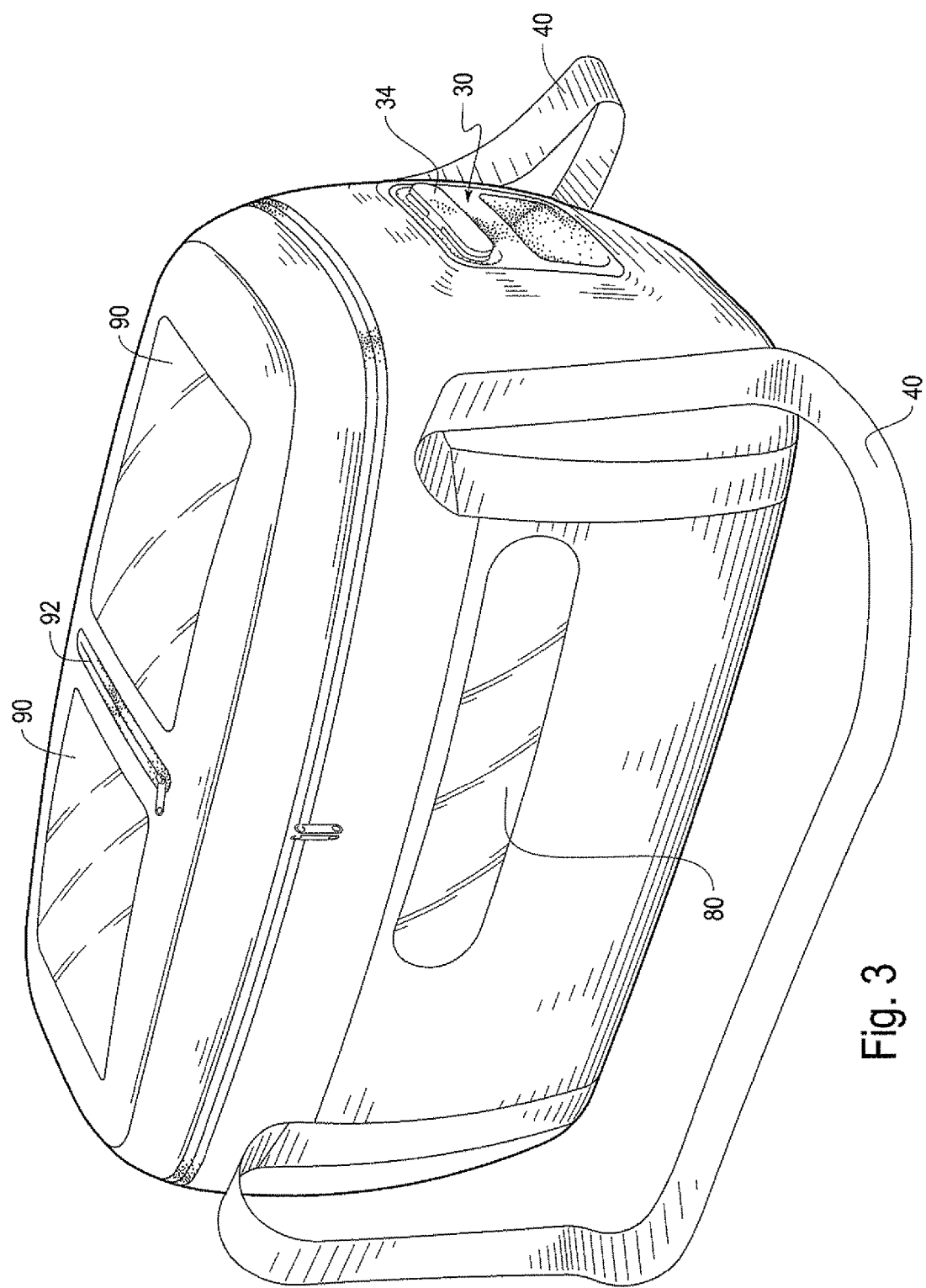
FIG. 3 illustrates a perspective view of a bag.
Figure 4:
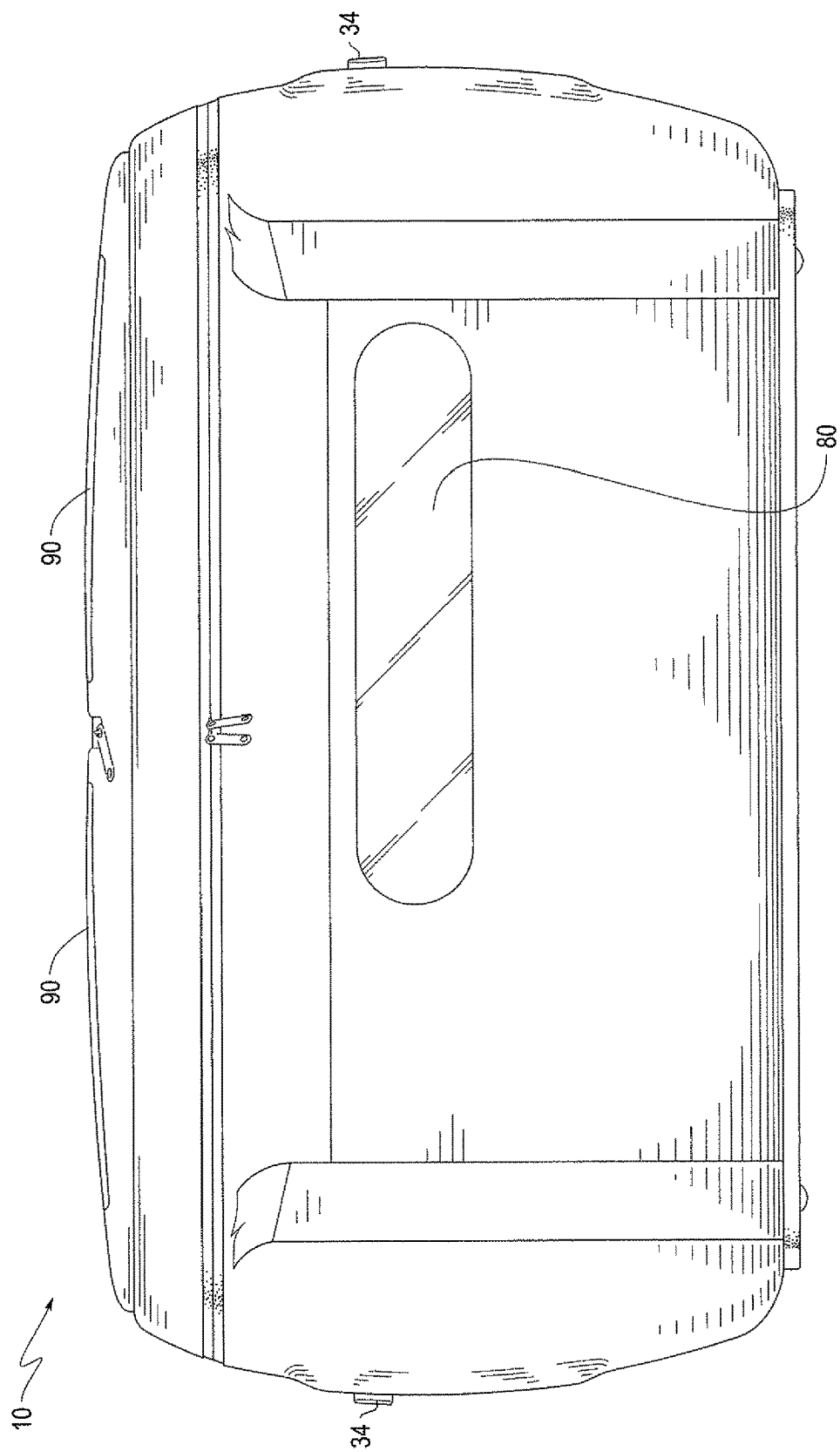
FIG. 4 illustrates a front view of a bag.
Figure 5:
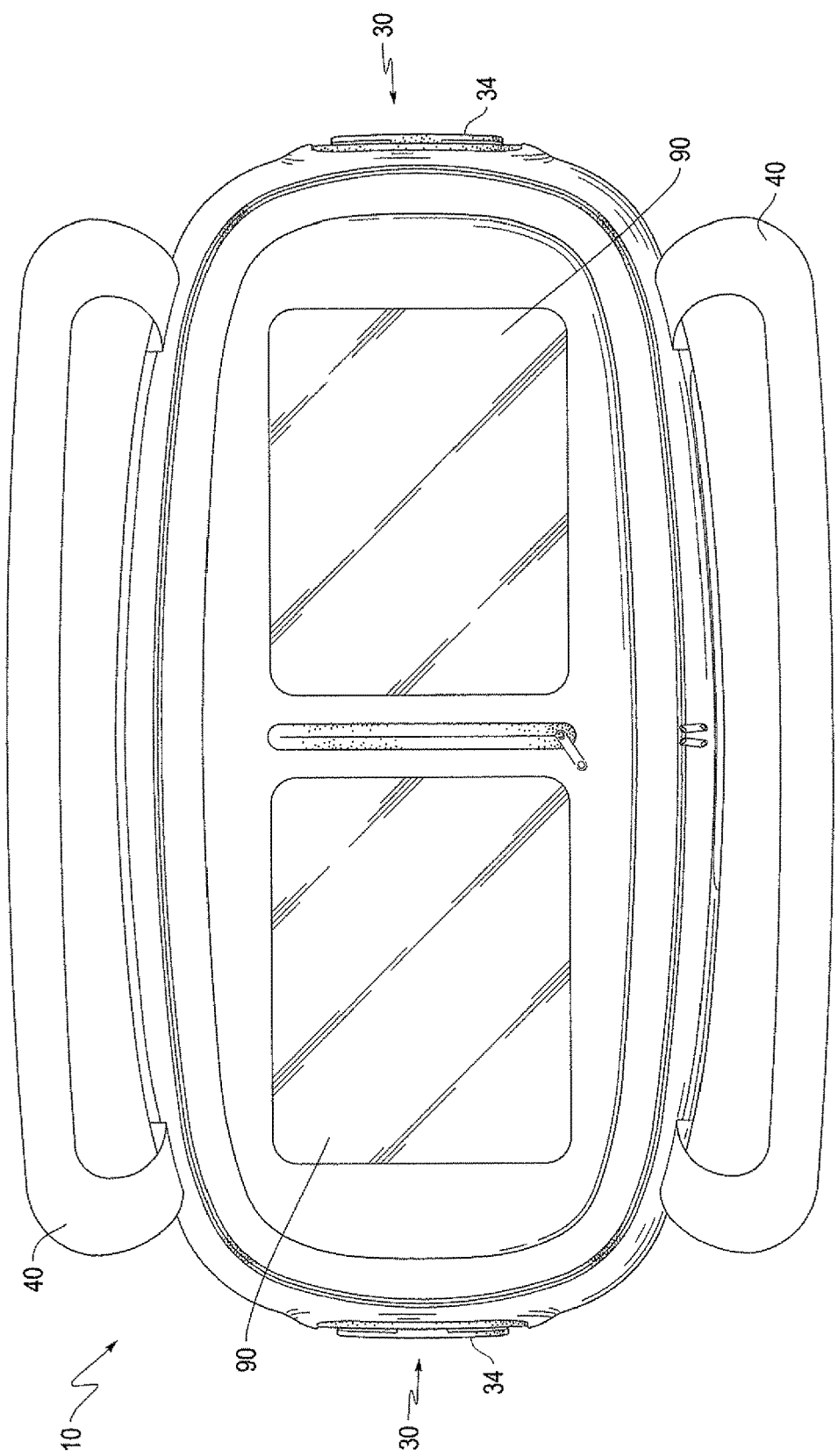
FIG. 5 illustrates a top view of a bag.
Figure 6:
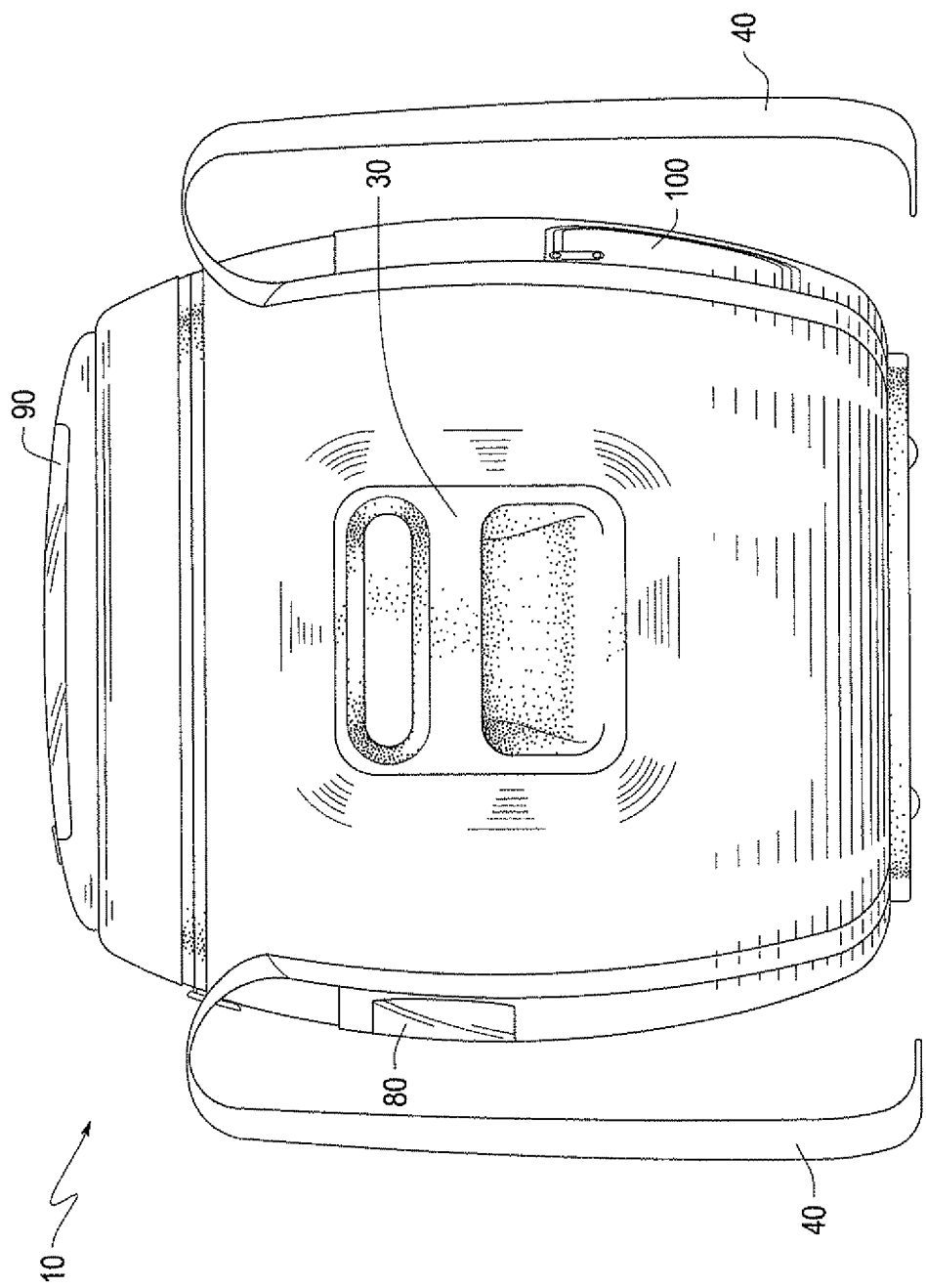
FIG. 6 illustrates a right side view of a bag.
Figure 7:
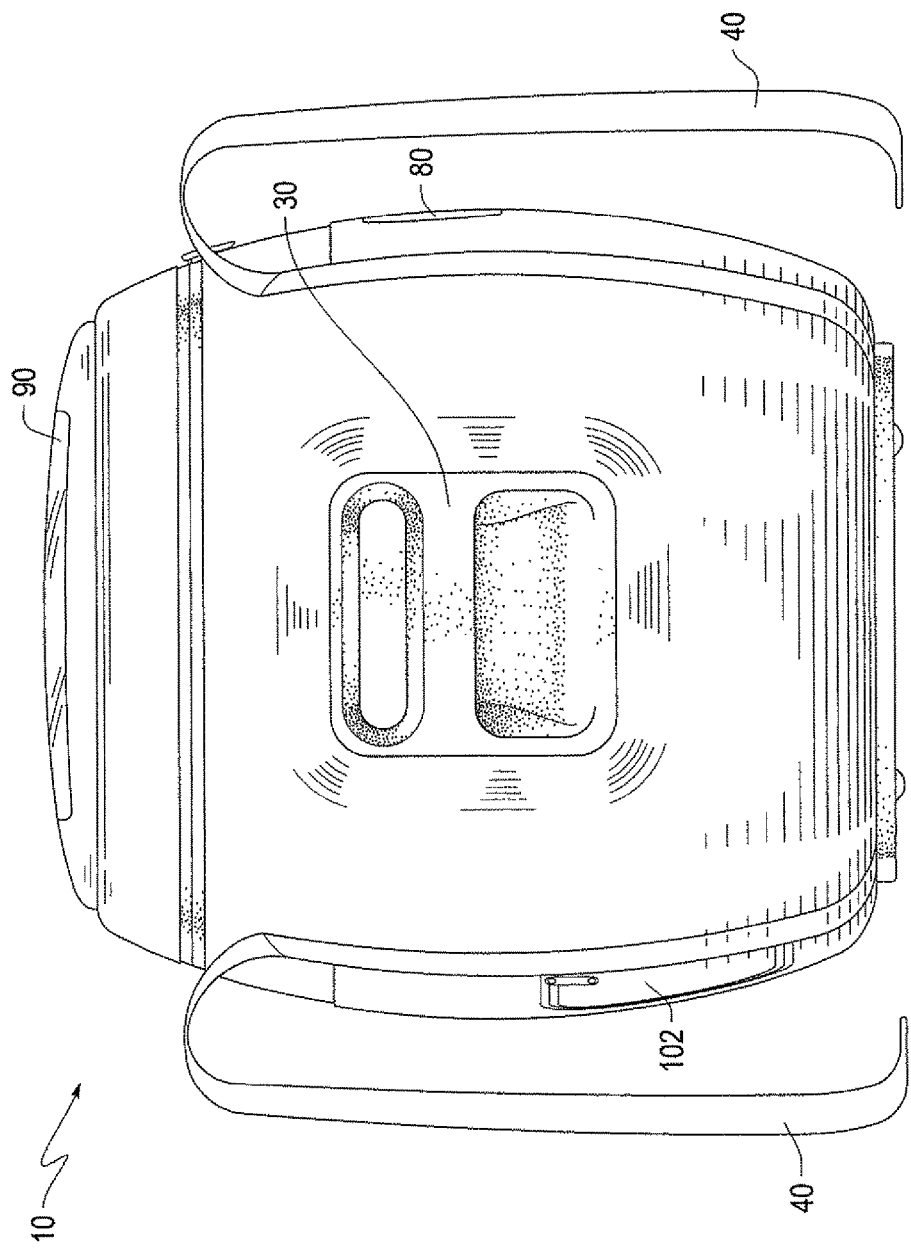
FIG. 7 illustrates a left side view of a bag.
Figure 8:
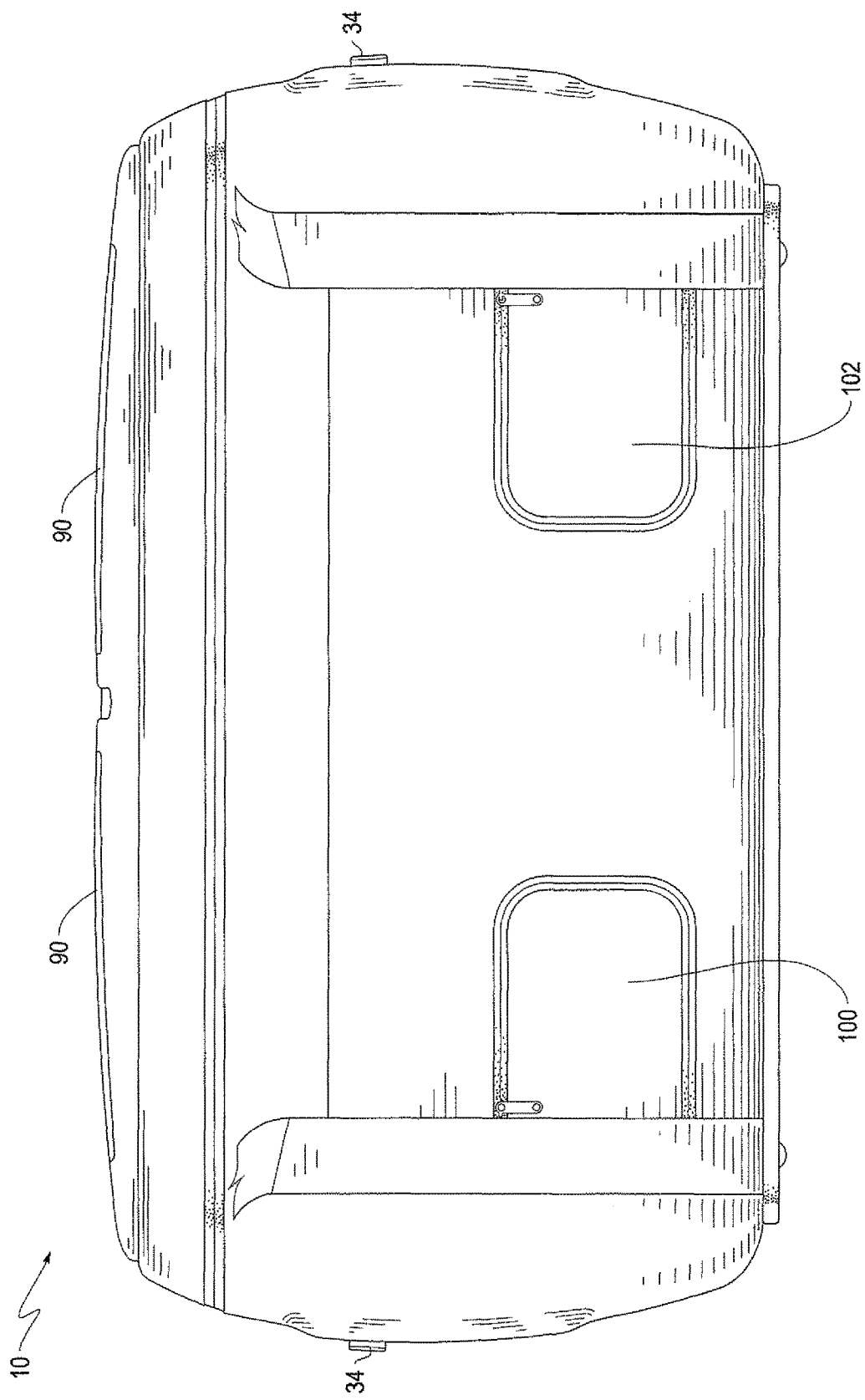
FIG. 8 illustrates a rear view of a bag.
Figure 9:
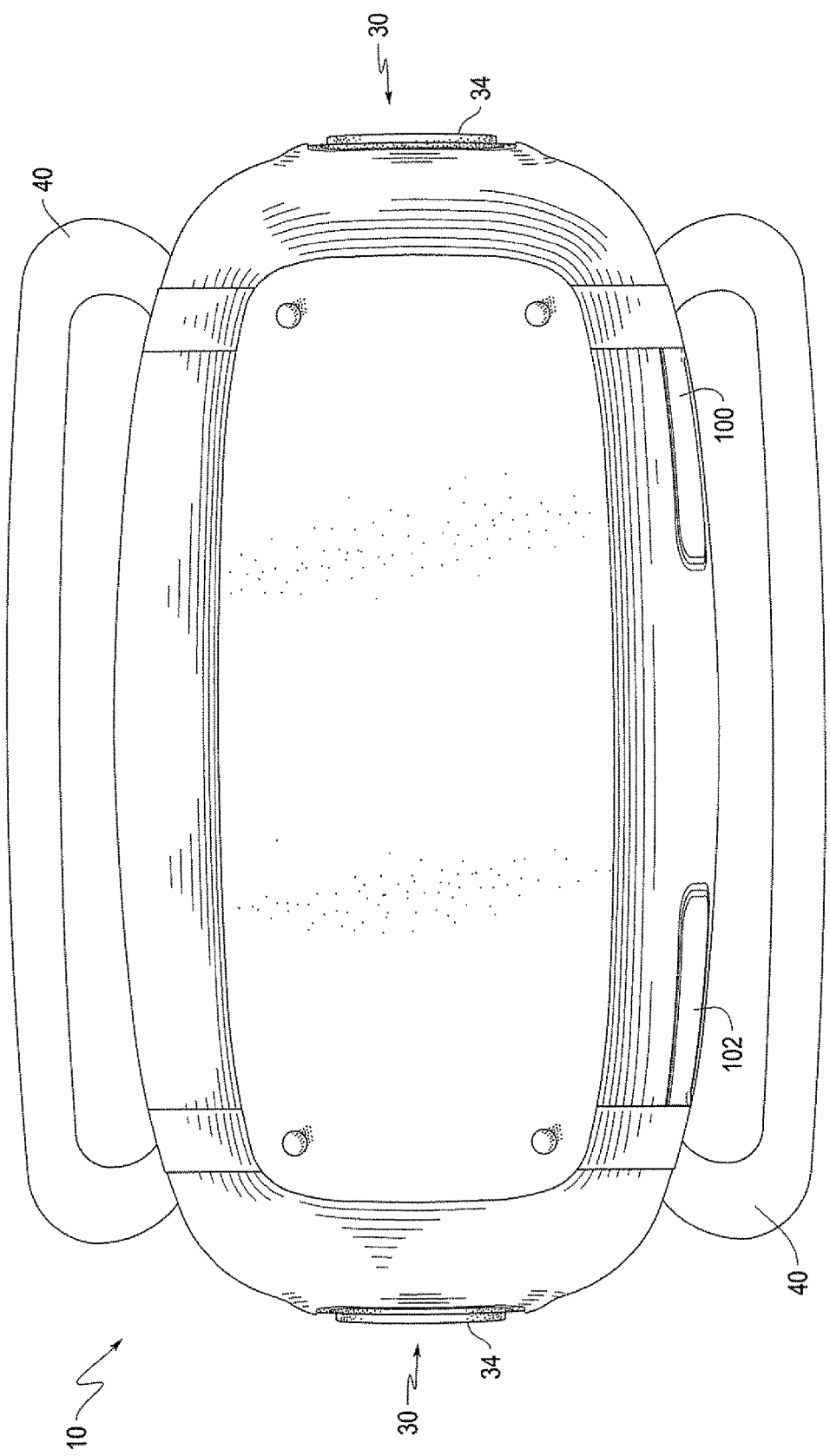
FIG. 9 illustrates a bottom view of a bag.

Between the two windows 90 visible in FIG. 3, a closure in the form of a zipper 92 is also shown. The zipper 92 is shown generally in the center of an outside surface of the cover 50, but any location and orientation may be implemented as dictated by the needs of a user and/or the documents (or other items) to be visible behind the windows 90. A corresponding closure or zipper may be included on an interior of the cover 50 (but is not visible in FIG. 1 because cover 52 is shown in the open position). Such a closure on the interior of the cover 50 may allow a user to readily access documents stored behind the windows 90 whether the cover 50 is in an open or a closed position. Alternatively, the zipper 90 or the interior closure may be omitted if it is preferred that access to the documents is only available from one side of the cover 50.

Although zippers are discussed above and illustrated throughout the figures (such as zipper 92 discussed above), any type of closure, such as hook and loop fabric, buttons, snaps or other devices for openably fastening or closing the covers, may be used. All of the zippers illustrated throughout the figures may be in the form of a double zipper that allows for the zipper handles to be locked together. Locking the zippers together can prevent unwanted access or can signal that the contents have been tampered with. In this regard, other tamper evident closures are contemplated by exemplary implementations disclosed herein FIG. 3 also shows a tie-down 34 that may be included as part of the handle 30 or separate from it. The tie-down 34 as shown is generally T-shaped and allows for the use of straps or cords to secure the bag 10 to a surface during transport. Of course, other shapes or configurations (such as a D-ring or other shaped ring) can be utilized for the tie-down 34 as well. Ventilation structure (not visible) may be provided preferably between the tie down 34 and the interior of the bag, to allow for the circulation of air into and out of the bag 10. Such ventilation structure may allow for hot air generated by heat from the organ transporter to escape from the bag, and for fresh air to enter. The ventilation structure may take any suitable form, such as one or more holes or a meshed material, that allows for adequate ventilation as dictated by the heat generated by the organ transporter 20 or by any other need for air to be circulated in the bag 10 and/or to the organ transporter 20.

FIGS. 6-9 show optional first access panel 100 and second access panel 102. Each of these access panels forms a closeable and openable cover for access into the bag 10. The organ transporter 20 may include a battery (not shown) that is accessible from an exterior of the organ transporter. In use, it may be necessary to replace a battery that has been depleted of its charge with a charged battery, but it is undesirable to have to remove the organ transporter 20 from the bag 10 in order to replace the battery. Thus, the first access panel 100 may be advantageously disposed to allow access to the battery for removal and replacement while maintaining the organ transporter 20 in the organ transporter compartment 60. Such a configuration may allow a battery to be changed without breaking a tamper seal on the cover 50 or the first inner cover 52. To achieve easy removal of the battery, the first access panel 100 may be shaped and/or aligned with the battery. The first access panel 100 may be slightly larger than the battery in order to minimize the size of the first access panel 100 while allowing the battery sufficient clearance to be easily removed.

The organ transporter may also include a power cord, circuit breakers, and/or a data cable (none of which are shown) in place of or in addition to the battery discussed above. The first access panel 100 or a second similar but optionally smaller access panel may be advantageously located to allow access to the power cord, circuit breakers, and/or a data cable. The access panel may be disposed such that the power cord, circuit breakers, and/or a data cable, or a plug for one or both of the power cord and/or the data cable, is uncovered when the access panel is open.

The second access panel 102 may be included to allow access to a further compartment (not shown) within the bag 10. The compartment may be used to store any items associated with the bag 10 or organ transporter 20, but preferably the compartment is configured to store the battery and/or power cord used with the organ transporter 20.

The functions of these access panels are dictated by items intended to be stored in the bag 10, but are otherwise interchangeable. For example, first access panel 100 allows for access to a battery of the organ transporter 10, and the position of the battery is dictated by the position of organ transporter 20 within the organ transporter compartment 60. However, if the organ transporter compartment 60, which is shown as being on a right-most portion of the bag 10 in FIG. 2, were instead disposed on a left-most portion of the bag 10, then the first access panel 100 would be correspondingly disposed.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. An organ transporter system, comprising:
   a bag comprising (i) a flexible or semi-rigid outer shell, (ii) an organ transporter compartment, (iii) a transparent window, (iv) two bag handles that are externally accessible, and (v) an internal frame connected to the two bag handles;
   an organ transporter disposed within the organ transporter compartment, the organ transporter comprising two transporter handles and including at least part of a perfusion circuit that is configured to perfuse an organ; and
   an outer cover that remains attached to the outer shell when the bag is in an open configuration and in a closed configuration,
   wherein:
   the transparent window is aligned with a display or control panel on the organ transporter to allow the display or control panel to be visible through the transparent window from an exterior of the bag,
   the organ transporter is disposed entirely within the bag when the bag is in the closed configuration, and
   at least one of the two bag handles mates with at least one of the two transporter handles when the organ transporter is disposed within the organ transporter compartment to transfer lifting force from the bag handle to the transporter handle.

2. The system according to claim 1, wherein
   the organ transporter comprises a battery that is accessible from an external surface of the organ transporter; and
   the bag comprises:
   a first opening configured to allow insertion and removal of the organ transporter into and from the organ transporter compartment; and
   a second opening configured to allow access to the battery while the organ transporter is disposed in the organ transporter compartment.

3. The system according to claim 2, wherein
   the organ transporter further comprises a power cord configured to supply power to the organ transporter; and
   the second opening is configured to allow the power cord to pass through the second opening while the organ transporter is disposed in the organ transporter compartment.

4. The system according to claim 2, wherein the first and second openings are separately openable and closeable.

5. The system according to claim 2, further comprising a second compartment separate from the organ transporter compartment, the second compartment being configured to store a battery for the organ transporter that is not installed in the organ transporter.

6. The system according to claim 5, wherein the second compartment is separately openable and closeable from the first and second openings.

7. The system according to claim 1, wherein
   the organ transporter comprises a power cord configured to supply power to the organ transporter; and
   the bag comprises:

a first opening configured to allow insertion and removal of the organ transporter from the organ transporter compartment; and a second opening configured to allow access to the power cord while the organ transporter is disposed in the organ transporter compartment.

8. The system according to claim 7, wherein the organ transporter further comprises a battery that is accessible from an external surface of the organ transporter; and the second opening is aligned with said surface to allow access to the battery while the organ transporter is disposed in the organ transporter compartment.

9. The system according to claim 1, wherein the two bag handles comprise tie-down elements that facilitate fastening the bag to an external structure through the use of tie-downs.

10. The system according to claim 9, wherein at least one of the two handles comprises a ventilation structure configured to allow ventilation air to be circulated to the organ transporter.

11. The system according to claim 10, wherein the ventilation structure extends between a corresponding one of the tie down elements and an interior of the organ transporter compartment.

12. The system according to claim 1, wherein:

the bag comprises:
  a sample compartment separate from the organ transporter compartment;
  a first closeable cover for the sample compartment; and
  a second closeable cover for the organ transporter compartment; and
the outer cover covers the first and second closeable covers.

13. The system according to claim 12, wherein the outer cover comprises:
  at least one cover compartment configured to store documents, the cover compartment including a closeable opening that is accessible from an interior of the outer cover; and
  a window adapted to display documents stored in the cover compartment, the window being visible when the outer cover is in a closed position.

14. The system according to claim 13, wherein the outer cover further comprises a second closeable opening that is accessible from an exterior of the outer cover.

15. The system according to claim 1, wherein the bag further comprises at least one flexible handle.

16. The system according to claim 1, wherein the two bag handles and the internal frame are rigidly connected.

17. The system according to claim 1, wherein the bag includes a battery that is configured to be used with the organ transporter to perfuse the organ but that is not installed in the organ transporter.

18. An organ transporter system, comprising:

an organ transporter comprising:
  a battery that is accessible from an external surface of the organ transporter,
  a power cord configured to supply power to the organ transporter,
  two transporter handles,
  a display on an external surface of the organ transporter, and
  a perfusion circuit that is configured to perfuse an organ; and a bag comprising:
  an organ transporter compartment that is configured to snugly accept the organ transporter,
  a transparent window aligned with the display to allow the display to be visible from an exterior of the bag when the organ transporter is disposed within the organ transporter compartment,
  a first opening configured to allow insertion and removal of the organ transporter into and from the organ transporter compartment,
  a second opening configured to allow access to the battery while the organ transporter is disposed in the organ transporter compartment and to allow access to the power cord while the organ transporter is disposed in the organ transporter compartment,
  a second compartment separate from the organ transporter compartment, the second compartment being configured to store a battery for the organ transporter that is not installed in the organ transporter, wherein the second compartment is separately openable and closeable from the first and second openings,
  two bag handles that are externally accessible and are configured to mate with handles on the transporter to transfer lifting force from the bag handles to the transporter handles,
  an internal frame,
  a sample compartment separate from the organ transporter compartment,
  a first closeable cover for the sample compartment,
  a second closeable cover for the organ transporter compartment, and
  a third closeable cover that covers the first and second closeable covers, the third closeable cover comprising:
    at least one cover compartment configured to store documents, the cover compartment including at least one closeable opening that is accessible from at least one of an interior of the third closeable cover and an exterior of the third closeable cover, and
    a window adapted to display documents stored in the cover compartment, the window being visible when the third closeable cover is in a closed position, and
  at least one flexible handle;

wherein:
  the two bag handles are rigidly connected to the internal frame,
  the two bag handles and the internal frame are rigid, and
  the first and second openings are separately openable and closeable.

* * * * *